United States Patent
Rathenow et al.

(10) Patent No.: US 7,371,425 B2
(45) Date of Patent: May 13, 2008

(54) METHOD FOR COATING SUBSTRATES WITH A CARBON-BASED MATERIAL

(75) Inventors: Jorg Rathenow, Eppstein (DE); Jurgen Kunstmann, Bad Soden (DE); Bernhard Mayer, Mainz (DE); Andreas Ban, Darmstadt (DE)

(73) Assignee: Cinvention AG (DE)

( * ) Notice: Subject to any disclaimer, the term of this patent is extended or adjusted under 35 U.S.C. 154(b) by 270 days.

(21) Appl. No.: 10/939,022

(22) Filed: Sep. 10, 2004

(65) Prior Publication Data
US 2005/0079356 A1  Apr. 14, 2005

Related U.S. Application Data

(63) Continuation-in-part of application No. PCT/EP2004/004987, filed on May 10, 2004.

(30) Foreign Application Priority Data

May 16, 2003 (DE) ............... 103 22 182
May 28, 2003 (DE) ............... 103 24 415

(51) Int. Cl.
B05D 3/04 (2006.01)

(52) U.S. Cl. ............... 427/2.24; 427/226

(58) Field of Classification Search ............... 427/2.24, 427/226
See application file for complete search history.

(56) References Cited

U.S. PATENT DOCUMENTS

| | | | |
|---|---|---|---|
| 3,623,164 A | 11/1971 | Bokros | |
| 3,685,059 A | 8/1972 | Bokros | |
| 3,775,078 A * | 11/1973 | Elmer et al. | 65/32.4 |
| 4,198,382 A | 4/1980 | Matsui | |
| 4,209,480 A | 6/1980 | Homsy | |
| 4,318,948 A | 3/1982 | Hodgson | |
| 4,759,977 A | 7/1988 | Fukuda et al. | |
| 4,986,943 A | 1/1991 | Sheaffer et al. | |
| 5,163,958 A | 11/1992 | Pinchuk | |
| 5,209,979 A | 5/1993 | Moehle et al. | |
| 5,326,510 A * | 7/1994 | Shinohara et al. | 264/29.1 |
| 5,352,486 A * | 10/1994 | Matsumoto et al. | 427/228 |
| 5,516,884 A | 5/1996 | Bianconi | |
| 5,597,617 A * | 1/1997 | DeLiso et al. | 427/228 |
| 5,891,507 A | 4/1999 | Jayaraman | |
| 5,912,048 A * | 6/1999 | Rao et al. | 427/228 |
| 6,024,899 A * | 2/2000 | Peng et al. | 264/29.1 |
| 6,355,350 B1 | 3/2002 | Guseva et al. | |
| 6,372,283 B1 | 4/2002 | Shim et al. | |
| 6,497,729 B1 | 12/2002 | Moussy et al. | |
| 6,544,582 B1 | 4/2003 | Yoe | |
| 6,569,107 B2 | 5/2003 | Jalisi et al. | |
| 6,859,986 B2 | 3/2005 | Jackson et al. | |
| 2003/0065355 A1 | 4/2003 | Weber | |
| 2004/0010108 A1 | 1/2004 | Bianconi et al. | |
| 2005/0067346 A1 | 3/2005 | Noack et al. | |

FOREIGN PATENT DOCUMENTS

| | | |
|---|---|---|
| DE | 22 24 614 | 12/1973 |
| DE | 26 13 072 | 10/1977 |
| DE | 32 04 700 | 9/1982 |
| DE | 39 02 856 | 8/1990 |
| DE | 197 30 296 | 1/1999 |
| DE | 199 51 477 | 5/2001 |
| DE | 100 51 910 | 5/2002 |
| EP | 0400938 A1 | 12/1990 |
| EP | 0731190 A1 | 9/1996 |
| EP | 1 306 096 | 5/2003 |
| GB | 1 163 422 | 9/1969 |
| GB | 1163442 A | 9/1969 |
| GB | 1 153 235 | 6/1978 |
| GB | 1513235 A | 9/1978 |
| JP | 61012918 A2 | 1/1986 |
| JP | 63050480 | 3/1988 |
| JP | 01222955 A2 | 9/1989 |
| JP | 05194056 A2 | 8/1993 |
| JP | 9110528 | 4/1997 |
| JP | 11172460 A2 | 6/1999 |
| WO | WO 97/43473 | 11/1997 |
| WO | WO 99/52838 | 10/1999 |
| WO | WO 99/64085 | 12/1999 |
| WO | WO9962571 A1 | 12/1999 |
| WO | WO0168158 A1 | 9/2001 |
| WO | WO 02/09791 | 2/2002 |
| WO | WO0232558 A1 | 4/2002 |
| WO | WO 02/080996 | 10/2002 |
| WO | WO02080996 A1 | 10/2002 |
| WO | WO2004101017 A2 | 11/2004 |

OTHER PUBLICATIONS

Bai Jinfeng et al., Study on Carbonization Conditions for a Pan-Based Hollow Fiber carbon Membrane, Journal of Fuel Chemistry and Technology, 1997 25(1)):85-89.

* cited by examiner

*Primary Examiner*—Fred J. Parker
(74) *Attorney, Agent, or Firm*—Frommer Lawrence & Haug LLP; Thomas J. Kowalski; Deborah L. Lu

(57) ABSTRACT

The present invention relates to a method for coating substrates with a carbon-based material, comprising the steps of at least partially coating a substrate with a polymer film on at least one outside surface of the substrate and carbonizing the polymer film in an atmosphere that is essentially free of oxygen at temperatures in the range of 200° C. to 2500° C.

12 Claims, No Drawings

METHOD FOR COATING SUBSTRATES WITH A CARBON-BASED MATERIAL

INCORPORATION BY REFERENCE

This application is a continuation-in-part application of international patent application Ser. No. PCT/EP2004/004987 filed May 10, 2004, which claims benefit of German patent application Ser. Nos. DE 103 22 182.4 filed May 16, 2003 and DE 103 24 415.8 filed May 28, 2003.

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention.

FIELD OF THE INVENTION

The present invention relates to a method for coating substrates with a carbon-based material by at least partially coating a substrate with a polymer film on at least one of its outside surfaces and then carbonizing the polymer film in an atmosphere that is substantially free of oxygen at temperatures in the range of 200° C. to 2500° C.

BACKGROUND OF THE INVENTION

Pyrolytic carbon has long been known as a very strong, abrasion-resistant material with a great range of variation in properties. Pyrolytic carbon is biocompatible because of its structure and composition, so it has long been used as a material or coating material in medical technology, in particular for producing medical implants of all types. Pyrolytic carbon with a turbostratic structure, optionally including silicon-alloyed carbon microcrystals, is used for coating stents and for the production of artificial heart valves, for example. U.S. Pat. No. 6,569,107 describes carbon-coated intraluminal stents to which the carbon material has been applied by means of chemical or physical vapor-phase deposition methods (CVD or PVD). German Patent DE 3902856 describes molded articles containing pyrocarbon produced by coking of carbon fiber articles, pyrocarbon infiltration and subsequent sealing of the surface with CVD carbon.

The deposition of pyrolytic carbon under PVD or CVD conditions requires a careful selection of suitable gaseous or vaporizable carbon precursors, which are deposited on a substrate at high temperatures, sometimes under plasma conditions, in an inert gas atmosphere or under a high vacuum. In addition, various in vacuo sputtering methods have been described in the state of the art for production of pyrolytic carbon of various structures (see U.S. Pat. No. 6,355,350, for example).

All these prior art methods have in common the fact that the deposition of carbon substrates takes place under extreme temperatures and/or pressure conditions with careful and complicated process control.

Furthermore, because of the different thermal expansion coefficients of the substrate material and the applied CVD carbon layer in the state of the art, frequently only a low adhesion of the layer to the substrate is achieved, resulting in flaking, cracking and a poor surface quality in general.

There has therefore been a demand for methods that are inexpensive and easy to use for coating substrates with a carbon-based material, such that these methods are capable of providing biocompatible surface coatings of a carbon material or carbon-coated substrates for microelectronic applications, for example.

Citation or identification of any document in this application is not an admission that such document is available as prior art to the present invention.

SUMMARY OF THE INVENTION

The object of the present invention is therefore to make available a method for coating substrates with a carbon-based material which uses inexpensive starting materials that are available in a wide variety and which also uses processing conditions that are easy to control.

Another object of the present invention is to make available substrates coated with a carbon-based material for use in medical technology, in particular for medical implants of a variety of types whose surface properties can be adapted to the particular intended purpose in a controlled manner accordingly.

Another object of the present invention is to provide a method for producing carbon-coated substrates for microelectronic purposes.

The inventive solution to the objects described above consists of a method for coating substrates with carbon-based material comprising at least partially coating a substrate with a polymer film on at least one of the outside surfaces of the substrate and carbonizing the polymer film in an atmosphere that is essentially free of oxygen at temperatures in the range of 200° C. to 2500° C.

Within the scope of the present invention, it has been found that carbon-coated products can be produced easily by first coating a substrate at least partially on the surface with a polymer film, which is then carbonized or pyrolyzed in an oxygen-free atmosphere at high temperatures.

Within the context of the present invention, carbonization or pyrolysis is understood to refer to partial thermal decomposition or coking of carbon-based starting compounds, usually polymer materials based on hydrocarbons which leave behind large amounts of amorphous carbon after undergoing carbonization.

It is noted that in this disclosure and particularly in the claims and/or paragraphs, terms such as "comprises", "comprised", "comprising" and the like can have the meaning attributed to it in U.S. patent law; e.g., they can mean "includes", "included", "including", and the like; and that terms such as "consisting essentially of" and "consists essentially of" have the meaning ascribed to them in U.S. patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

DETAILED DESCRIPTION

The substrates that can be used according to this invention may include all the substantially temperature-resistant materials, i.e., materials that are stable and preferably retain their shape under the carbonization conditions and/or pyrolysis conditions that are used. Examples of substrates that can be used according to this invention include, but are not limited to, metals, alloys, ceramics, graphite, glass, stone, carbon fiber materials, carbon fiber composite materials, minerals, bone substance and imitation bone based on calcium carbonate and the like.

The use of ceramic greenware as a substrate is also advantageously possible according to this invention because it can be sintered in parallel to form a finished ceramic while the coating is undergoing carbonization. For example, it is possible to use conventional commercial and traditional ceramics (boron nitride, silicon carbide, etc.) or nanocrystalline greenware of zirconium oxide and $\alpha$- or $\gamma$-$Al_2O_3$ or pressed amorphous nanoscale AlOOH aerogel, which lead to nanoporous carbon-coated molded articles at temperatures of approximately 500-2000° C., but preferably approximately 800° C., which yield coatings with a porosity of approximately 10 nm to 100 nm.

The inventive method yields coatings that have an extremely high mechanical load capability and in particular it solves the delamination problem with traditional coated substrates, which tend to abrasion of coatings applied secondarily under severe mechanical torsion, tensile and strain loads.

The materials used for substrates coated according to this invention, in particular those for medical purposes, include all the materials conventionally used in the medical and dental fields, such as metals, e.g., titanium, platinum, palladium, gold, alloys, e.g., cobalt-chromium alloys, low-porosity graphite, polymers, carbon fiber implants, ceramics such as calcium phosphate ceramics, zeolites, aluminum oxides, apatite ceramics and the like, although this list is not intended to be complete.

The substrates may have virtually any external form if they can be coated with a polymer film on at least one of their exterior surfaces. Preferred examples of substrates that can be used according to this invention include, but are not limited to, medical implants such as prostheses and joint replacements, bone implants, artificial hip joints and hip-bone implants, devices that can be used intraluminally such as stents, e.g., metal stents such as nitinol stents, polymer stents, surgical orthopedic aids such as bone screws, nails, plates and the like.

In preferred embodiments of the present invention, the substrates to be coated include stents, in particular metal stents.

Other examples of substrates that can be used according to this invention include, but are not limited to, components from the field of microelectronics and micromechanics, construction materials such as, but not limited to, metal ceramics in glass and stone and carbon fiber composite materials, Raschig rings, Sulzer packings, cartridge systems and filter systems, insulation materials and the like.

The temperature-resistant substrates are coated at least partially on at least one of their outside surfaces by the method according to this invention. In certain preferred applications, e.g., in medical devices, they are usually coated over their entire outside surface with one or more polymer films.

In one embodiment of this invention, the polymer film may be in the form of a polymer foil which is applied to the substrate by film shrinking methods, for example, or can be glued to the substrate. Thermoplastic polymer foils can be applied adherently to most substrates even when heated.

Suitable films consist of homo or copolymers of aliphatic or aromatic polyolefins such as, but not limited to, polyethylene, polypropylene, polybutene, polyisobutene, polypentene, polybutadiene, polyvinyls such as polyvinyl chloride or polyvinyl alcohol, poly(meth)acrylic acid, polyacrylonitrile, polyamide, polyester, polyurethane, polystyrene, polytetrafluorethylene, waxes, paraffin waxes, Fischer-Tropsch waxes, mixtures and combinations of these homopolymers and copolymers and the like.

In preferred embodiments, polymer films and coatings based on foamed polymers such as, but not limited to, foamed polyolefins, phenolic foams, polystyrene foams, foamed polyurethane, fluoropolymer foams and the like may be used to advantage. These have the advantage that it is possible to produce coatings with a pore structure that is adjustable as a function of the foam porosity in the carbonization step. To produce the foamed polymers, all the conventional state-of-the-art foaming methods may be used, wherein conventional blowing agents such as halohydrocarbons and low-boiling hydrocarbons are used.

According to another embodiment of the present invention, the polymer film may also include a coating of the substrate selected from lacquers or laminates. Preferred coatings can be produced by superficial parylenation of the substrates. In this process the substrates are first treated with paracyclophane at an elevated temperature, usually approximately 600° C., forming a polymer film of poly-(p-xylylene) at the surface of the substrate. This film can then be converted to carbon in a subsequent carbonization or pyrolysis step.

In preferred embodiments, the sequence of parylenation and carbonization will be repeated several times.

Suitable lacquer-based polymer films may be produced, for example, from a lacquer which includes a binder base of alkyd resin, fluorinated rubber, epoxy resin, acrylic resin, phenolic resin, amine resin, an oil base, a nitro base, polyester, polyurethane, tar, tar-like materials, tar pitch, bitumen, starch, cellulose, shellac, organic materials of renewable raw materials or combinations thereof.

In the inventive method, several layers of the aforementioned polymer films may be applied to the implant and then carbonized jointly. By using different polymer film materials, optional additives in individual polymer films or films of varying thickness, gradient coatings may thus be applied to the implant in a controlled manner, e.g., with variable porosity profiles or adsorption profiles within the coatings. Furthermore, the sequence of polymer film coating and carbonization may be repeated once or optionally even multiple times to produce carbon-based multilayer coatings on the implant. The polymer films or substrates may be prestructured or modified by using additives. Suitable after-treatment steps such as those described below may be used after each step or after individual sequences of steps in polymer film coating and carbonization by the method according to this invention such as an oxidative treatment of individual layers.

Using polymer films coated with the lacquers or coating solutions mentioned above to coat the implants, e.g., by means of lamination techniques such as, but not limited to, thermal methods, compression methods or wet-in-wet methods is also possible advantageously according to this invention.

In certain embodiments of the present invention, the polymer film may be furnished with additives which influence the carbonization performance of the film and/or the macroscopic properties of the carbon-based substrate coating resulting from the method. Examples of suitable additives include, but are not limited to, fillers, pore-forming agents, metals and metal powders, etc. Examples of inorganic additives and fillers include, but are not limited to, silicon oxides and aluminum oxides, aluminosilicates, zeolites, zirconium oxides, titanium oxides, talc, graphite, carbon black, fullerenes, clay materials, phyllosilicates, silicides, nitrides, metal powders, in particular those of catalytically active transition metals such as copper, gold and silver, titanium, zirconium, hafnium, vanadium, niobium, tantalum, chromium, molybdenum, tungsten, manganese, rhenium, iron, cobalt, nickel, ruthenium, rhodium, palladium, osmium, iridium or platinum.

By means of such additives in the polymer film, it is possible to vary and adjust the biological, mechanical and thermal properties of the films, for example, as well as the resulting carbon coatings. For example, the thermal expansion coefficient of the carbon layer can be adapted to that of a substrate of ceramic by incorporating layered silicates, so that the applied carbon-based coating adheres well even when exposed to great temperature differences. Adding aluminum-based fillers results in an increase in the thermal expansion coefficient and adding glass-, graphite- or quartz-based fillers yields a reduction in the thermal expansion coefficient, so that by mixing the components in the polymer system, it is possible to adjust the thermal expansion coefficient on an individual basis accordingly. Another possible adjustment of properties can be accomplished, for example but not exclusively by producing a fiber composite by adding carbon fibers, polymer fibers, glass fibers or other fibers in a woven or nonwoven form, which results in a definite increase in elasticity of the coating.

Polymer films have the advantage that they can be obtained commercially or they are easily produced in virtually any desired dimensions. Polymer foils are readily available, inexpensive, and can be applied easily to a wide variety of different types of substrates. The polymer films used according to this invention may be structured in a suitable way before pyrolysis and/or carbonization by folding, embossing, punching, pressing, extruding, gathering, injection molding and the like before or after being applied to the substrate. In this way, certain structures of a regular or irregular type can be incorporated into the carbon coating produced by the method according to this invention.

The polymer films of coatings in the form of lacquers or other coatings that can be used according to this invention may be applied to the substrate from a liquid, slurry or pasty state, e.g., by spreading, painting, lacquering, dispersion coating or melt coating, extruding, casting, dipping or as a hot melt from the solid state by means of powder coating, comb spray coating, sintering or the like by essentially known methods. Lamination of suitably shaped substrates with polymer materials or foils suitable for this purpose is also a method that can be used according to this invention for coating the substrate with a polymer film.

Especially preferably in the coating of substrates with polymer films, application of the poly and/or a solution thereof by printing methods such as those described in German Patent DE 10351150, the disclosure content of which is fully herewith incorporated by reference. This method permits in particular a precise and reproducible adjustment of the layer thickness of the applied polymer material.

The polymer film applied to the substrate is optionally dried and then subjected to a pyrolytic decomposition under carbonization conditions in which the polymer film applied as a coating to the substrate is carbonized at an elevated temperature in an essentially oxygen-free atmosphere. The temperature of the carbonization step is preferably in the range of 200° C. to 2500° C. and is selected by those skilled in the art as a function of the specific temperature-dependent properties of the polymer films and substrates used.

Preferred temperatures for the carbonization step that can be used in general in the process according to this invention are from approximately 200° C. to approximately 1200° C. In some embodiments, temperatures in the range of 250° C. to 700° C. are preferred. In general the temperature is selected according to the properties of the materials used, so that the polymer film is converted essentially completely to a carbon-based solid at the lowest possible temperature. Through a suitable choice and/or control of the pyrolysis temperature, the porosity, strength and stiffness of the material as well as other properties can be adjusted in a controlled manner.

Porosity is preferably produced in the inventive layers on implants by treatment methods such as those described in German Patent DE 103 35 131 and PCT/EP04/00077, the complete disclosure content of which is herewith fully incorporated by reference.

By using very high temperatures up to 2000° C. or more, carbon-based coatings in a graphitic form can be produced according to this invention. A suitable choice of the carbonization temperature allows controlled adjustment of the crystallinity of the coatings from completely amorphous at low temperatures to highly crystalline at high temperatures. Thus the mechanical properties of the coatings can also be adjusted and optimized in a controlled manner according to the particular intended application.

The atmosphere in the carbonization step of the inventive method is essentially free of oxygen. It is preferable to use inert gas atmospheres, e.g., comprising nitrogen, noble gases such as argon, neon and any other inert gases or gas compounds that do not react with carbon as well as mixtures of inert gases is preferred. Nitrogen and/or argon are preferred.

Carbonization is usually performed at normal pressure in the presence of inert gases such as those mentioned above. If necessary, however, higher inert gas pressures may also be used advantageously. In certain embodiments of the inventive method, carbonization may also be performed at a reduced pressure, i.e., in vacuo.

The pyrolysis step is preferably performed in a continuous furnace process. The optionally structured, coated or pretreated polymer films are fed into the furnace on one side and emerge from the furnace again at the other end. In preferred embodiments, the polymer film and/or the object made of polymer films may rest on a perforated plate, a screen or the like in the furnace, so that the polymer film can be placed under pressure during the pyrolysis and/or carbonization process. This permits not only a simple means of fixation of the objects in the furnace but also a suction effect and optionally also a flow of inert gas through the films and/or components during pyrolysis and/or carbonization.

The furnace may be subdivided into individual segments through corresponding inert gas locks so that one or more pyrolysis steps and/or carbonization steps can be carried out in these individual segments, optionally under different pyrolysis and/or carbonization conditions such as different temperature levels, different inert gases and/or in vacuo.

Furthermore, aftertreatment steps such as secondary activation may optionally also be performed in corresponding segments of the furnace by reduction or oxidation or impregnation with metal salt solutions, etc.

As an alternative to this, the pyrolysis/carbonization may also be performed in a closed furnace, which is preferred in particular when the pyrolysis and/or carbonization is to be performed in vacuo.

During pyrolysis and/or carbonization in the inventive method, the polymer film usually shows a weight loss of approximately 5% to 95%, preferably approximately 40% to 90%, in particular 50% to 70%, depending on the starting material used and the pretreatment. In addition, shrinkage of the polymer film and/or the structure and/or component produced from polymer films usually occurs during pyrolysis and/or carbonization in the inventive process. This shrinkage may be on the order of 0% to approximately 95%, preferably 10% to 30%.

In the inventive method, the electric conductivity of the coating may be adjusted in a wide range, depending on the pyrolysis and/or carbonization temperature used and the type and amount of the additive and/or filler material used. This is advantageous in particular for applications in microelectronics. Thus a higher conductivity can be achieved at temperatures in the range of 1000° C. to 2500° C. due to the graphitization of the coating that occurs in comparison with that at lower temperatures. In addition, however, the electric conductivity may also be increased, e.g., by adding graphite to the polymer film, which can then be pyrolized and/or carbonized at a lower temperature. Such modified coated substrates are suitable for the production of sensors, for example.

The carbon-based coating produced according to this invention has a carbon content of at least 1 wt % (percent by weight, preferably at least 25 wt %, optionally also at least 60 wt % and in particular preferably at least 75 wt %, depending on the starting material and the type and amount of filler materials. Coatings that are especially preferred according to this invention have a carbon content of at least 50 wt %.

In preferred embodiments of the inventive method, the physical and chemical properties of the resulting carbon-based coating of the substrate can be further modified after carbonization through suitable aftertreatment steps and adapted to the desired application in each case.

The properties of the porous carbon-based coating obtained after pyrolysis and/or carbonization can be influenced in a controlled manner and refined by coating the polymer film on one or both sides with epoxy resins, phenolic resin, tar, tar pitch, bitumen, rubber, polychloroprene or poly(styrene-co-butadiene) latex materials, siloxanes, silicates, metal salts and/or metal salt solutions, e.g., transition metal salts, carbon black, fullerenes, activated carbon powder, carbon molecular sieve, perovskite, aluminum oxides, silicon oxides, silicon carbide, boron nitride, silicon nitride, noble metal powders such as Pt, Pd, Au or Ag as well as combinations thereof or through targeted incorporation of such materials into the polymer film structure; in addition, multilayer coatings can also be produced. The thermal expansion coefficient as well as the mechanical properties of the resulting carbon coatings can be modified, for example, by incorporating layered silicates, nanoparticles or inorganic nanocomposites, into the polymer film or by coating the polymer film with layered silicates, metals, metal oxides and the like.

In the inventive production of coated substrates, there is the possibility of improving the adhesion of the applied layer to the substrate by incorporation of the additives mentioned above into the polymer film and there is the possibility, for example, of adjusting the thermal expansion coefficient of the outer layer to that of the substrate so that these coated substrates are more resistant to cracking and flaking of the coating. These coatings are thus more durable and have a greater long-term stability in the concrete application than do traditional products of this type.

Applying or incorporating metals and metal salts, in particular also noble metals and transition metals, makes it possible to adapt the chemical, biological and adsorptive properties of the resulting carbon-based coatings to the desired requirements in each case so that the resulting coating can also be equipped with heterogeneous catalytic properties for special applications, for example.

In preferred embodiments of the inventive method, the physical and chemical properties of the carbon-based coating are further modified after pyrolysis and/or carbonization by suitable aftertreatment steps and adapted to the intended application in each case.

Suitable aftertreatments include, for example, reducing or oxidative aftertreatment steps in which the coating is treated with suitable reducing agents and/or oxidizing agents such as hydrogen, carbon dioxide, steam, oxygen, air, nitric acid and the like plus optionally mixtures thereof.

The aftertreatment steps may optionally be performed at an elevated temperature, but below the pyrolysis temperature, e.g., 40° C. to 1000° C., preferably 70° C. to 900° C., especially preferably 100° C. to 850° C., most especially preferably 200° C. to 800° C. and in particular at approximately 700° C. In especially preferred embodiments, the coating produced according to this invention is modified by reduction or oxidation or with a combination of these aftertreatment steps at room temperature.

By oxidative or reductive treatment or by the incorporation of additives, fillers or functional materials, the surface properties of the coatings produced according to this invention can be influenced and/or modified in a controlled manner. For example, by incorporating inorganic nanoparticles or nanocomposites such as layered silicates, it is possible to impart hydrophilic or hydrophobic properties to the surface of the coating.

Furthermore, the surface properties of the coated substrate can be modified by ion implantation. For example, by implanting nitrogen, it is possible to form nitride, carbonitride or oxynitride phases with incorporated transition metals, which definitely increases the chemical resistance and mechanical resistance of the carbon-based coatings. Implantation of carbon ions can result in an increase in the mechanical strength of the coatings and can be used for postcompression of porous layers.

The coatings produced according to this invention can also be furnished subsequently with biocompatible surfaces by incorporating suitable additives and may optionally be used as bioreactors or drug vehicles. To do so, medications or enzymes may be introduced into the material, for example, in which case the former can be released in a controlled manner through a suitable delayed release formulation and/or selective permeation properties of the coatings.

Furthermore in certain embodiments it is preferable to perform fluoridation of the coatings produced according to this invention, e.g., to enable surface-coated stents to uptake lipophilic substances and/or active ingredients.

By the method according to this invention it is also possible to suitably modify the coating on the substrate, e.g., by varying the pore sizes by means of suitable aftertreatment steps such that the carbon-based coating facilitates or promotes the growth of microorganisms or viable cells. Suitably coated substrates may then be used as a growth medium for microorganisms in bioreactors, for example. The porosity of the coating may be adjusted advantageously so that the supply of nutrients to cells or microorganisms populating the external surfaces can be ensured through nutrient depots or active ingredient depots situated on the substrate, with the nutrients going from the substrate to the microorganism population at the surface by permeation through the carbon-based coating.

The carbonized coating may optionally also be subjected to a so-called CVD process (chemical vapor deposition) in another optional process step to further modify the surface structure or the pore structure and the properties thereof. This is done by treating the carbonized coating with suitable precursor gases at high temperatures. Such methods have long been known in the state of the art.

Almost all the known saturated and unsaturated carbons having a sufficient volatility under CVD conditions may be used as the precursors to split off carbon. Examples include methane, ethane, ethylene, acetylene, linear and branched alkanes, alkenes and alkynes with carbon numbers of $C_1$-$C_{20}$, aromatic hydrocarbons such as benzene, naphthalene, etc., as well as aromatics with one or more alkyl, alkenyl and alkynyl substituents such as toluene, xylene, cresol, styrene, etc.

Ceramic precursors that may be used include $BCl_3$, $NH_3$, silanes such as tetraethoxysilane (TEOS), $SiH_4$, dichlorodimethylsilane (DDS), methyltrichlorosilane (MTS), trichlorosilyl-dichloroborane (TDADB), hexadichloromethylsilyl oxide (HDMSO), $AlCl_3$, $TiCl_3$ or mixtures thereof.

These precursors are usually used in CVD processes in a low concentration of approximately 0.5 vol % to 15 vol % in mixture with an inert gas such as nitrogen, argon or the like. Hydrogen may also be added to suitable gas separation mixtures. At temperatures between 500° C. and 2000° C., preferably 500° C. to 1500° C. and especially preferably 700° C. to 1300° C., these compounds split off hydrocarbon fragments and/or carbon or ceramic precursors, which are deposited essentially uniformly in the pore system of the pyrolyzed coating, where they modify the pore structure and thus lead to an essentially homogeneous pore size and pore distribution in the sense of further optimization.

The carbon-based coatings produced according to this invention have extraordinarily good mechanical strength. Inventive coatings on stainless steel (e.g., 316L) usually have a modulus of elasticity of approximately 10-30 GPa, a Vickers hardness of approximately 200 to 600, typically approximately 400 and friction coefficients of approximately 0.03 to 0.2, typically approximately 0.14. Fractures in the layer are observed only above approximately 30-60 N (scratch adhesion); abrasion is observed above approximately 40 mN to 400 mN.

Pyrolytic carbon is usually a material with a high biocompatibility which can be used for medical applications such as for external coating of implants. The biocompatibility of the substrates coated according to this invention can also be influenced and/or altered as mentioned above in a controlled manner by incorporating additives, fillers, proteins or functional materials and/or medications into the polymer films before performing carbonization. In this way, rejection reactions in the body can be reduced or prevented entirely when using implants produced according to this invention.

In especially preferred embodiments, carbon-coated medical implants produced according to this invention can be used for controlled release of active ingredients from the substrate into the external environment through controlled adjustment of the porosity of the applied carbon layer. In this way, medical implants, for example, can be used as drug vehicles with a depot effect, whereby the carbon-based coating of the implant can be used as a membrane to regulate the release of the active ingredient. Drugs may also be applied to biocompatible coatings. This is useful in particular in cases where active ingredients cannot be applied in or to the substrate directly as is the case with metals.

Furthermore, the coatings produced according to this invention can be loaded with drugs, i.e., medication in another process step or may also be loaded with markers, contrast agents for localizing coated implants in the body or with therapeutic or diagnostic quantities of radioactive isotopes. For the latter, the inventive carbon-based coatings are especially suitable because in contrast with polymer layers, they are not affected or attacked by radiation.

In the medical field, implants coated according to this invention have proven to have especially great long-term stability because the carbon-based coatings not only have a high strength but also have sufficient elasticity and flexibility so that they can conform to the movements of the implant, in particular in the case of joints that are under high stresses, without there being any risk of cracks developing or the layer flaking off.

This invention will now be explained in greater detail on the basis of examples representing preferred embodiments which do not reflect any necessary restrictions of the invention as described in the claims:

EXAMPLES

Example 1

Carbon

A carbon material coated according to this invention was prepared as follows. A polymer film was applied to paper with a grammage of 38 g/m² as the greenware by coating the paper repeatedly with a commercial epoxidized phenolic resin lacquer using a doctor blade and then drying at room temperature; dry weight 125 g/m². Pyrolysis at 800° C. for 48 hours under nitrogen yielded carbon sheeting having an asymmetrical structure and the following dimensions with a shrinkage of 20% and a weight loss of 57%: total thickness 50 micrometers, a dense carbon-based layer according to this invention with a thickness of 10 micrometers on an open-pore carbon substrate with a thickness of 40 micrometers, formed in situ from the paper under the pyrolysis conditions. The absorption capacity of the coated carbon material was up to 18 g ethanol/m².

Example 2

Glass

Duroplan® glass was subjected to 15 minutes of an ultrasonic cleaning in a water bath containing a surfactant, then rinsed with distilled water and acetone and dried. This material was coated by dip coating with a conventional packing lacquer based on phenolic resin in an application weight of $2.0 \times 10^{-4}$ g/cm². After subsequent carbonization at 800° C. for 48 hours under nitrogen, the coating showed a weight loss to $0.33 \times 10^{-4}$ g/cm². The coating which was previously colorless then turned a shiny black and was hardly transparent anymore after carbonization. The hardness of the coating was tested by drawing a pencil over the coated surface with a 1 kg weight at an angle of 45°, resulting in no visibly perceptible damage to the surface up to a hardness of 5H.

Example 3

Glass CVD Coating

Comparative Example

Duroplan® glass was subjected to a 15-minute ultrasonic cleaning, rinsed with distilled water and acetone and then dried. This material was coated with $0.05 \times 10^{-4}$ g/cm² carbon by chemical vapor deposition (CVD) by bringing benzene at 30° C. in a bubbler with a nitrogen flow in contact with the glass surface at 1000° C. for 30 minutes and depositing it as a film on the glass surface. The previously colorless glass surface would then turn a shiny gray and was transparent after the deposition. A test of the hardness of the coating with a pencil drawn at an angle of 45° with a 1 kg weight over the coated surface did not reveal any visibly perceptible damage to the surface up to a hardness of 6 B.

Example 4

Glass Fiber

Duroplan® glass fibers with a diameter of 200 micrometers are subjected to an ultrasonic cleaning for 15 minutes, then rinsed with distilled water and acetone and dried. This material is then coated by dip coating with a commercial packing lacquer with an application weight of $2.0 \times 10^{-4}$ g/cm². After subsequent pyrolysis and carbonization at 800° C. for 48 hours, the coating shows a weight loss to $0.033 \times 10^{-4}$ g/cm². The previously colorless coating becomes shiny black and is hardly transparent at all after carbonization. A test of adhesion by bending in a 180° radium does not cause any flaking, i.e., visibly perceptible damage to the surface.

Example 5

Stainless Steel

Stainless steel number 1.4301 in the form of a 0.1 mm foil (Goodfellow) is subjected to an ultrasonic cleaning for 15 minutes, rinsed with distilled water and acetone and dried. This material is then coated with a conventional packing lacquer in an application weight of $2.0 \times 10^{-4}$ g/cm² by dip coating. After subsequent pyrolysis and carbonization at 800° C. for 48 hours under nitrogen, the coating shows a weight loss to $0.49 \times 10^{-4}$ g/cm². The previously colorless coating becomes a matte black after carbonization. A test of the coating hardness will a pencil drawn at an angle of 45° with a 1 kg weight over the coated surface yields no visibly perceptible damage to the surface up to a hardness of 4B. An adhesive strip pull-away test (in which a Tesa® tape strip at least 3 cm long is glued to the surface by pressing with the thumb for 60 seconds and then pulled away from the surface at an angle of 90°) reveals hardly any adhesion.

Example 6

Stainless Steel, CVD Coating

Comparative Example

Stainless steel number 1.4301 has a 0.1 mm foil (Goodfellow) is subjected to an ultrasonic cleaning for 15 minutes, rinsed with distilled water and acetone and dried. This material is then coated by chemical vapor deposition (CVD) in an amount of $0.20 \times 10^{-4}$ g/cm². To do so, benzene at 30° C. in a bubbler with a nitrogen flow is brought in contact with the hot metal surface at 1000° C. so that it is broken down at the high temperatures and is deposited as a film on the metal surface. The previously metallic surface becomes shiny black after this deposition. A test of the hardness of the coating using a pencil drawn at a 45° angle with a 1 kg weight over the coated surface reveals no visibly perceptible damage to the surface up to a hardness of 4B.

A Tesa® adhesive film pull-away test in which a Tesa® strip of adhesive tape at least 3 cm long is pressed against the surface with the thumb for 60 seconds and then pulled away from the surface again at a 90° angle reveals clearly visible gray adhesions.

Example 7

Titanium

Titanium 99.6% as a 0.1 mm foil (Goodfellow) is subjected to an ultrasonic treatment for 15 minutes, rinsed with distilled water and acetone and dried. This material is coated with a commercial packing lacquer in the amount of $2.2 \times 10^{-4}$ g/cm² by dip coating. After subsequent pyrolysis and carbonization at 800° C. for 48 hours under nitrogen, the coating shows a weight loss to $0.73 \times 10^{-4}$ g/cm². The previously colorless coating becomes a matte, shiny gray-black. A test of the coating hardness with a pencil drawn at a 45° angle with a 1 kg weight over the coated surface reveals no visual damage to the surface up to a hardness of 8H. For example, the coating cannot scraped off with a paperclip. A pull-away test in which a Tesa® strip of tape at least 3 cm long is pressed against the surface with the thumb for 60 seconds and then pulled away at an angle of 90° from the surface does not reveal any adhesions.

Example 8

Titanium, Finished with CVD

Titanium 99.6% as a 1 mm film (Goodfellow) is subjected to a 15-minute ultrasonic cleaning, rinsed with distilled water and acetone and dried. This material is coated with a commercial packing lacquer in the amount of $2.2 \times 10^{-4}$ g/cm². After subsequent pyrolysis with carbonization at 800° C. for 48 hours under nitrogen, the coating shows a weight loss to $0.73 \times 10^{-4}$ g/cm². This material is coated further with $0.10 \times 10^{-4}$ g/cm² by chemical vapor deposition (CVD). To do so, benzene at 30° C. in a bubbler with nitrogen flow is brought in contact with the hot coated metal surface for 30 minutes at 1000° C., then decomposes and is deposited as a film on the surface. The previously metallic surface becomes shiny black after this deposition. After cooling to 400° C., the surface is oxidized by passing air over it for a period of three hours. A test of the hardness of the coating using a pencil drawn at a 45° angle with a 1 kg weight over the coated surface reveals no visibly perceptible damage to the surface up to a hardness of 8H. A pull-away test in which a Tesa® adhesive tape strip at least 3 cm long is pressed with the thumb against the surface for 60 seconds and then pulled away from the surface again at a 90° angle reveals gray material adhering to the tape.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

The invention claimed is:

1. A method for coating substrates with carbon-based material comprising the following steps: a) at least partially coating of a substrate with a polymer film comprising a polymer foil on at least one of the outside surfaces of the substrate, b) applying the polymer foil to the outside surfaces of the substrate by film shrinking methods or b) adhering the polymer foil to the outside surfaces of the substrate, and c) carbonizing the polymer film in an atmosphere that is essentially free of oxygen at temperatures in the range of 200° C. to 2500° C.

2. The method according to claim 1 wherein the polymer film further comprises additives selected from the group consisting of fillers, pore-forming agents, metals, extenders, lubricants and pigments.

3. The method according to claim 2 wherein the additives are selected from the group consisting of silicon oxides, aluminum oxides, aluminosilicates, zirconium oxides, titanium oxides, talc, graphite, carbon black, zeolite, clay minerals, phyllosilicates, fullerenes, catalysts, metals and metal compounds.

4. The method according to claim 1 wherein the polymer foil comprises one or more compounds selected from the group consisting of homopolymers, homopolymers of aliphatic polyolefins, homopolymers of aromatic polyolefins, copolymers, copolymers of aromatic polyolefins, copolymers of aliphatic polyolefins and mixtures thereof.

5. The method according to claim 1 wherein the polymer film further comprises lacquers, laminates and coatings.

6. The method according to claim 5 wherein the polymer film further comprises a lacquer film produced from a lacquer with a binder base of alkyd resin, chlorinated rubber, epoxy resin, acrylate resin, phenolic resin, amine resin, oil base, nitro base, polyester, polyurethane, tar, tar pitch, bitumen, starch, cellulose, shellac, waxes, organic materials of renewable raw materials or combinations thereof.

7. The method according to claim 1 wherein the carbon-based material is subjected to an oxidative and/or reductive aftertreatment following carbonization and is optionally subjected to a CVD procedure for deposition of carbon and/or a ceramic.

8. The method according to claim 1 wherein the substrate is selected from a group consisting of metals, alloys, ceramics, zeolite, graphite, glass, stone, sand, carbon fiber composites, bone materials, bone substitutes, minerals, precursors, ceramic greenware and combinations thereof.

9. The method according to claim 1 wherein the substrate is selected from medical implants, stents or catalyst supports.

10. The method according to claim 1 wherein the coated substrate further comprises active ingredients or microorganisms.

11. The method according to claim 10 wherein the applied active ingredients are released through controlled adjustment of the porosity of the carbon coating.

12. The method according to claim 1 wherein the polymer foil comprises polyethylene, polypropylene, polybutene, polyisobutene, polypentene, polybutadiene, polyvinyls, polyvinyl chloride, polyvinyl alcohol, poly(meth)acrylic acid, polyacrylonitrile, polyamide, polyester, polyurethane, polystyrene, polytetrafluoroethylene, waxes, paraffin waxes, Fischer-Tropsch waxes or mixtures thereof.

* * * * *